(12) United States Patent
Kromm et al.

(10) Patent No.: US 8,501,985 B2
(45) Date of Patent: Aug. 6, 2013

(54) USE OF PHOSPHONIUM SALTS IN COUPLING REACTIONS AND PROCESS FOR THEIR MANUFACTURE

(75) Inventors: Klemenz Kromm, Köln (DE); Jan Haller, Leverkusen (DE)

(73) Assignee: Dynamit Nobel GmbH Explosivstoff-und Systemtechnik, Leverkusen (DE)

( * ) Notice: Subject to any disclaimer, the term of this patent is extended or adjusted under 35 U.S.C. 154(b) by 677 days.

(21) Appl. No.: 12/670,056

(22) PCT Filed: Jul. 25, 2008

(86) PCT No.: PCT/IB2008/002774
§ 371 (c)(1),
(2), (4) Date: Jan. 21, 2010

(87) PCT Pub. No.: WO2009/013628
PCT Pub. Date: Jan. 29, 2009

(65) Prior Publication Data
US 2010/0197969 A1    Aug. 5, 2010

(30) Foreign Application Priority Data

Jul. 26, 2007  (EP) .................................. 07014681

(51) Int. Cl.
*C07F 9/54*            (2006.01)
(52) U.S. Cl.
USPC ................................. 562/9; 562/24
(58) Field of Classification Search
USPC ...................................... 562/9, 24
See application file for complete search history.

(56) References Cited

FOREIGN PATENT DOCUMENTS

| EP | 1657259 A1 | 5/2006 |
| EP | 1712572 A1 | 10/2006 |
| WO | 02085843 A2 | 10/2002 |
| WO | 2004098772 A2 | 11/2004 |

*Primary Examiner* — Shawquia Young
(74) *Attorney, Agent, or Firm* — Marsh Fischmann & Breyfogle LLP

(57) ABSTRACT

The object of the present invention is the use of phosphonium salts in coupling reactions, and a method for their preparation.

15 Claims, No Drawings

USE OF PHOSPHONIUM SALTS IN COUPLING REACTIONS AND PROCESS FOR THEIR MANUFACTURE

FIELD OF THE INVENTION

The present invention relates to the use of phosphonium salts in coupling reactions and to a process for their manufacture.

BACKGROUND OF THE INVENTION

Many reagents catalyzed by palladium or other transition metals require phosphine ligands (I. Ojima (publisher), *Catalytic Asymmetric Synthesis*, VCH, New York, Weinheim 1993; E. Negishi (publisher), *Handbook of Organopalladium Chemistry for Organic Synthesis*, Wiley-Interscience, New York 2002; M. Beller, C. Bolm (publisher), *Transition Metals for Organic Synthesis*, Wiley-VCH, Weinheim 1998; N. J. Whitcombe, K. K. Hii, S. E. Gibson, *Tetrahedron* 2001, 57, 7449-7476; D. Prim, J.-M. Campagne, D. Joseph, B. Andrioletti, *Tetrahedron* 2002, 58, 2041-2075; A. F. Littke, G. C. Fu, *Angew. Chem.* 2002, 114, 4350-4386). These often have the disadvantage, especially with regard to trialkylphosphines, to oxidize very easily in air, thereby becoming useless, or even pyrophoric (K. Sasse (publisher), *Houben-Weyl, Methods of Organic Chemistry*, 4$^{th}$ Edition, Volume XII/1, p. 69, Georg-Thieme-Verlag, Stuttgart 1963).

The problem with the oxidation sensitivity of phosphines can be bypassed by producing tetrafluoroborate salts from them, and they can be used as ligand precursors for catalysis reactions (M. R. Netherton, G. C. Fu, *Org. Lett.* 2001, 3, 4295-4298; S. Eichenseher, K. Kromm, O. Delacroix, J. A. Gladysz, *Chem. Commun.* 2002, 1046-1047). Tetrafluoroborates were selected, because this anion does not have a coordinating effect, and therefore has no adverse effect on the catalysis reaction. However, it was shown that trialkylphosphonium tetrafluoroborates have a strong corrosive effect. For example, tricyclohexyl phosphonium tetrafluoroborate has such a strong corrosive effect that a glazed porcelain bowl, in which the substance was dried, became matte due to the effect of the fluoride released from this substance. The use of this substance, for example, should therefore be avoided in enameled pans and glass lined vessels.

Also previously described are:

The preparation of trialkylphosphonium chlorides (K. L. Tan, S. Park, J. A. Ellman, R. G. Bergman, *J. Org. Chem.* 2004, 69, 7329-7335); these are very hygroscopic, and must be handled under inert gas.

The preparation of trialkylphosphonium tetraphenylborates (D. G. Gusev, R. Hübener, P. Burger, O. Orama, H. Berke, *J. Am. Chem. Soc.* 1997, 119, 3716-3731); however, tetraphenylborates as counterions are not available inexpensively.

Chiral diphosphine salts with at least one phospholane group (WO-A-2004/098772), as non-, or little hygroscopic and stable when exposed to air catalyst ligand precursors; the bismethanesulfonate of RoPHOS (1,2-bis[(2S,3S,4S,5S)-3,4-bis(benzyloxy)-2,5-dimethylphospholanyl]benzene) is very hygroscopic, and not stable when exposed to air.

The preparation of air stable bisphosphonium salts with sterogenic centers at the phosphor atoms, and trifluoromethane sulfonate as counterions from the borane adduct of phosphates (H. Danjo, W. Sasaki, T. Miyazaki, T. Imamoto, *Tetrahedron Lett.* 2003, 44, 3467-3469).

The $^{31}$P-NMR spectrum of a solution of tributylphosphonium trifluoromethane sulfonate in methylene chloride at −70° C. (P. Kubisa, S. Penczek, *Makromol. Chem.* 1979, 180, 1821-1823). The isolation of the salt is not described.

The protonation enthalpies of various phosphines with trifluoromethane sulfonic acid (R. J. Anelici, *Acc. Chem. Res.* 1995, 28, 51-60). The isolation of the salts is not described.

The enthalpy of formation of fluorinated trialkylphosphonium trifluoromethane sulfonates and their $^{31}$P-NMR spectra (H. Jiao, S. Le Stang, T. Soós, R. Meier, K. Kowski, P. Rademacher, L. Jafarpour, J.-B. Hamard, S. Nolan, J. A. Gladysz, *J. Am. Chem. Soc.* 2002, 124, 1516-1523 The isolation of the salts is not described.

The $^{1}$J($^{31}$P-$^{1}$H) coupling constant of various phosphonium sulfonates prepared only as a solution in fluorosulfonic acid (F. Krech, A. Zschunke, *Z. inorg. Chem.* 1978, 440, 45-51).

A Heck reaction known in the literature with tricyclohexylphosphine or tri-tert-butylphosphine as the catalyst ligand (WO-A-02/085843; R. A. Singer, J. D. McKinley, G. Barbe, R. A. Farlow *Org. Lett.* 2004, 6, 2357-2360); express reference is made to the sensitivity to air of tricyclohexylphosphine: the phosphine should only be used from freshly opened vessels. This will hamper stock-piling, which requires that either containers must be filled with the required amount, or that residual amounts not to be used must be discarded.

WO-A-2004/098772 discloses the use of phospholane salts in enantioselective hydrogenation. Notably this document discloses the use of triflates and tetrafluoroborates of phospholanes as being non-hydroscopic while the mesylate is found to be very hygroscopic.

Thus the aim of the present invention is to provide phosphonium salts that overcome the disadvantages of the compounds described in prior art, in particular, they should not be corrosive, while at the same time remain non-, or only little hygroscopic.

SUMMARY OF THE INVENTION

The invention thus provides the use of phosphonium salts as set forth in claim 1 while dependent claims provide specific embodiments The invention further provides a process for manufacturing the salts according to claim 12 while dependent claims provide specific embodiments

DETAILED DESCRIPTION OF PREFERRED EMBODIMENTS

The salts according to the invention are surprisingly not corrosive, compared with the tetrafluoroborates, while at the same time are non hygroscopic. The salts as used in the invention can form an active catalyst with a transition metal, without poisoning the same. The salts of the invention are also not explosive.

The salts according to the invention are sulfonates and/or carboxylates of monophosphines of the type PR$^1$R$^2$R$^3$*ZR'.

In this regard, it is understood as follows, in the invention:

Cy as cyclohexyl;

t-Bu as tert-butyl;

the residues R, R$^1$, R$^2$, R$^3$ as H and/or alkyl, cycloalkyl, aryl and/or hetaryl residues; wherein hydrogen atoms may be substituted in the alkyl, cycloalkyl, aryl and/or hetaryl residues;

Z as —SO$_3$H or —COOH;

the residue R' for Z=—SO$_3$H as alkyl, cycloalkyl, aryl, hetaryl residue or halogen; in particular fluorine, hydrogen atoms may be substituted in the alkyl, cycloalkyl, aryl and/or hetaryl residues, preferably by halogen;

the residue R' for Z=—COOH as H or alkyl, cycloalkyl, aryl or hetaryl residue; hydrogen atoms may be substituted in the alkyl, cycloalkyl, aryl and/or hetaryl residues, preferably by halogen;

the residue R as alkyl, cycloalkyl, aryl- or hetaryl residue; wherein hydrogen atoms may be substituted, in particular R is selected from the residues methyl, ethyl, propyl, isopropyl, butyl, sec-butyl, tert-butyl, isobutyl, cyclohexyl, phenyl, and/or methylphenyl;

X as halogen, preferably as fluoride;

X$^1$, X$^2$, X$^3$ as halogen, preferably as chlorine and/or bromine, as OR and/or NR$_2$ residue;

M as metal, preferably as lithium or magnesium;

Y as anion;

m as a number from 1 to 6, n as a number from 0 to 4, o as a number from 0 to 5;

R, R$^1$, R$^2$, R$^3$ and R' may be the same or different. X$^1$, X$^2$, X$^3$ may be the same or different.

It was further surprisingly found that the salts according to the invention can be prepared easily by precipitating them from the crude product solution of their synthesis without the associated phosphine first being isolated in its pure form, or in crystalline form as an adduct with a Lewis acid.

In the instant invention, the associated phosphines can be prepared, for example, by Grignard-like or by alkyllithium reactions, or by producing the conversions of phosphine with alkenes without limiting the invention to such.

It was further surprisingly found that the salts according to the invention can be used in reactions, in which according to the prior art only the free phosphine, or the tetrafluoroborate is used. According to the prior art the counterion is first removed, because it interferes with the reaction. According to the invention it is surprisingly only necessary in some cases to use a base in order to release the phosphine in situ, however without having to remove the counterion. In many of these reactions a stoichiometric amount of base, such as a metal alcoholate, in particular sodium-tert-butylate, or an amine is used.

The invention relates in more details to:

a monophosphonium salt of the type PR$^1$R$^2$R$^3$*ZR';

a monophosphonium salt of the type PR$^1$R$^2$R$^3$*ZR', wherein the residues R$^1$, R$^2$, and R$^3$ are selected from H and/or alkyl, cycloalkyl, aryl and/or hetaryl residues; in particular R$^1$, R$^2$, R$^3$ are selected from H and/or one or more of the residues methyl, ethyl, propyl, isopropyl, butyl, sec-butyl, tert-butyl, isobutyl, cyclopentyl, cyclohexyl, phenyl, and/or methylphenyl;

a monophosphonium salt of the type PR$^1$R$^2$R$^3$*ZR', wherein the residues R$^1$, R$^2$, and R$^3$ are selected from alkyl and/or cycloalkyl residues; in particular R$^1$, R$^2$, R$^3$ are selected from H and/or one or more of the residues methyl, ethyl, propyl, isopropyl, butyl, sec-butyl, tert-butyl, isobutyl, cyclopentyl and/or cyclohexyl;

a monophosphonium salt of the type PR$^1$R$^2$R$^3$*ZR', wherein the cycloalkyl residue is a cyclohexyl residue;

a monophosphonium salt of the type PR$^1$R$^2$R$^3$*ZR', wherein the alkyl residue is a tert-butyl residue;

a monophosphonium salt of the type PR$^1$R$^2$R$^3$*ZR', wherein Z is selected from —SO$_3$H or —COOH, preferably —SO$_3$H.

a monophosphonium salt of the type PR$^1$R$^2$R$^3$*ZR', wherein the residue R' for Z=—SO$_3$H is selected from alkyl, cycloalkyl, aryl, hetaryl residues, or a halogen, in particular fluorine; hydrogen atoms may be substituted in the alkyl, cycloalkyl, aryl and/or hetaryl residues, preferably by halogen, particularly preferably by fluoride, in particular R' is selected from fluoride, and/or the residues methyl, trifluoromethyl, ethyl, propyl, isopropyl, butyl, sec-butyl, tert-butyl, isobutyl, cyclohexyl, phenyl, and/or methylphenyl;

a monophosphonium salt of the type PR$^1$R$^2$R$^3$*ZR', wherein the residue R' for Z=—COOH is selected from the H or alkyl, cycloalkyl, aryl or hetaryl residues; hydrogen atoms may be substituted in the alkyl, cycloalkyl, aryl, and/or hetaryl residues, preferably by halogen, especially preferably by fluoride, in particular R' is selected from H and/or from the residues methyl, trifluoromethyl, ethyl, propyl, isopropyl, butyl, sec-butyl, tert-butyl, isobutyl, cyclohexyl, phenyl, and/or methylphenyl;

a monophosphonium salt of the type PR$^1$R$^2$R$^3$*ZR', wherein it is tricyclohexylphosphonium trifluoromethane sulfonate;

a monophosphonium salt of the type PR$^1$R$^2$R$^3$*ZR', wherein it is tricyclohexylphosphonium methane sulfonate;

a monophosphonium salt of the type PR$^1$R$^2$R$^3$*ZR', wherein it is tricyclohexylphosphonium-p-toluene sulfonate;

a monophosphonium salt of the type PR$^1$R$^2$R$^3$*ZR', wherein it is tricyclohexylphosphonium trifluoroacetate;

a monophosphonium salt of the type PR$^1$R$^2$R$^3$*ZR', wherein it is tri-tert-butylphosphonium trifluoromethane sulfonate;

a monophosphonium salt of the type PR$^1$R$^2$R$^3$*ZR', wherein it is tri-tert-butylphosphonium methane sulfonate;

a monophosphonium salt of the type PR$^1$R$^2$R$^3$*ZR', wherein it is tri-tert-butylphosphonium-p-toluene sulfonate;

a monophosphonium salt of the type PR$^1$R$^2$R$^3$*ZR', wherein it is tri-tert-butylphosphonium trifluoroacetate;

a method for the preparation of a monophosphonium salt of the type PR$^1$R$^2$R$^3$*ZR', wherein it is obtained by means of conversion of a phosphine of the type PR$^1$R$^2$R$^3$ with an acid of the type ZR';

a method for the preparation of a monophosphonium salt of the type PR$^1$R$^2$R$^3$*ZR', wherein the acid is selected from methane sulfonic acid, trifluoromethane sulfonic acid, or p-toluene sulfonic acid, or trifluoroacetic acid;

a method for the preparation of a monophosphonium salt of the type PR$^1$R$^2$R$^3$*ZR', wherein the conversion occurs in a solvent;

a method for the preparation of a monophosphonium salt of the type PR$^1$R$^2$R$^3$*ZR', wherein the phosphine PR$^1$R$^2$R$^3$ is obtained by means of conversion of a compound of the type PX$^1$X$^2$X$^3$ with a compound of the type $(R_mM)^{n+}(Y_o)^{n-}$;

a method for the preparation of a monophosphonium salt of the type PR$^1$R$^2$R$^3$*ZR' by means of conversion of a compound of the type PX$^1$X$^2$X$^3$ with a compound of the type $(R_mM)^{n+}(Y_o)^{n-}$, wherein PX$^1$X$^2$X$^3$ is a phosphorus trihalogenide, preferably phosphorus trichloride or phosphorus tribromide;

a method for the preparation of a monophosphonium salt of the type PR$^1$R$^2$R$^3$*ZR' by means of conversion of a compound of the type PX$^1$X$^2$X$^3$ with a compound of the type $(R_mM)^{n+}(Y_o)^{n-}$, wherein the compound of the type $(R_mM)^{n+}(Y_o)^{n-}$ is a Grignard compound;

a method for the preparation of a monophosphonium salt of the type $PR^1R^2R^{3*}ZR'$ by means of conversion of a compound of the type $PX^1X^2X^3$ with a compound of the type $(R_mM)^{n+}(Y_o)^{n-}$, wherein the compound of the type $(R_mM)^{n+}(Y_o)^{n-}$ is a lithium-organic compound;

a method for the preparation of a monophosphonium salt of the type $PR^1R^2R^{3*}ZR'$, wherein the phosphine is prepared by means of conversion of phosphane ($PH_3$) with an alkene;

a method for the preparation of a monophosphonium salt of the type $PR^1R^2R^{3*}ZR'$, wherein the phosphine is released from an adduct with a Lewis acid;

a method for the preparation of a monophosphonium salt of the type $PR^1R^2R^{3*}ZR'$ from an adduct with a Lewis acid, wherein the Lewis acid is carbon disulfide or borane;

a method for the preparation of a monophosphonium salt of the type $PR^1R^2R^{3*}ZR'$ from an adduct with a Lewis acid, wherein the Lewis acid is carbon disulfide or borane;

a method for the preparation of the phosphonium of the type $PR^1R^2R^{3*}ZR'$ wherein the phosphine is not isolated after its synthesis but the phosphonium salt is precipitated directly from the reaction mixture by addition of the acid ZR'; The neat phosphine or its solution are air sensitive and their isolation for later handling is always an issue. The instant process avoids the intermediate isolating step.

a method for preparing a phosphonium salt of disclosed above, by converting a phosphine of the type $PR^1R^2R^3$ with an acid of the type ZR' without prior isolating the phosphine; preferably wherein the. phosphonium salt precipitates from the crude product solution of the phosphine synthesis further to the addition of the acid ZR'.

the use of a monophosphonium salt of the type $PR^1R^2R^{3*}ZR'$ in chemical reactions together with one or more transition metals, and/or their compounds, wherein the transition metals are selected from one or more of the elements of the seventh and eighth subgroup of the periodic table;

the use of a monophosphonium salt of the type $PR^1R^2R^{3*}ZR'$ in chemical reactions together with one or more transition metals, and/or their compounds, wherein the transition metals are selected from one or more of the group of rhenium, ruthenium, rhodium, palladium, osmium, iridium, or platinum;

the use of a monophosphonium salt of the type $PR^1R^2R^{3*}ZR'$ in chemical reactions together with one or more transition metals, and/or their compounds, wherein the phosphine from the phosphonium salt is released by means of adding a base, preferably by adding a metal alcoholate, especially preferably by adding sodium-tert-butylate, or by adding a basic amine especially a tertiary amine such as triethylamine.

the coupling reactions are Buchwald, Heck, Negishi, Stille, Sonogashira. or Suzuki reactions.

The present invention provides phosphonium salts that are not sensitive to oxidation. The phosphonium salts are preferably non-, or only little hygroscopic, i.e. remain free flowing, even under the influence of air humidity. The phosphonium salts are not pyrophoric, or even explosive. There is no inhibiting effect of the second component in the phosphine adduct as catalyst ligand, no prior treatment is required. The phosphonium salts are easy to produce, and are used as ligands or ligand precursors for catalysts for coupling reactions.

The following examples illustrate the invention without limiting it.

EXAMPLES

Example 1

Preparation of Tricyclohexyl Phosphonium Trifluoromethane Sulfonate ($PCy_3T$, $PCy_3*F_3CSO_3H$, $C_{19}H_{34}F_3O_3PS$)

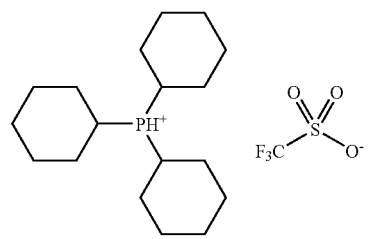

36.3 g cyclohexylchloride is dissolved in 120 ml diethylether. 25 ml of this solution and 0.2 ml 1,2-dibromoethane are added to 7.7 g of magnesium turnings. The temperature rises to 39° C. The remaining cyclohexylchloride solution is added to the mixture at a slight reflux, and the mixture is subsequently held at reflux for one hour. The Grignard solution is cooled down to room temperature, decanted from the excess magnesium, and added to a solution of 12.6 g phosphorus trichloride in 35 ml diethylether at −15 to −10° C. in 75 min. The reaction mixture is stirred at reflux for one hour, and subsequently added to 72 ml 15% ammonium chloride solution at 3 to 16° C. After adding 47 ml water the lower aqueous phase is separated, and the upper ethereal tricyclohexyl phosphine solution is further processed. The product solution is cooled down to 10° C., and 14.1 g trifluoromethane sulfonic acid are added within 20 minutes. The resulting suspension is stirred for one hour at 10° C., the product is filtered off, washed with 30 ml diethylether, and dried at 40° C. 24.9 g (64%) tricyclohexyl phosphonium trifluoromethane sulfonate is obtained as a yellowish-white solid. The reaction is schematically illustrated below:

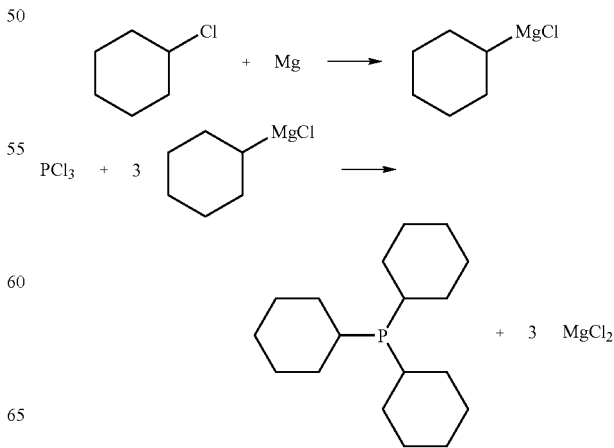

-continued

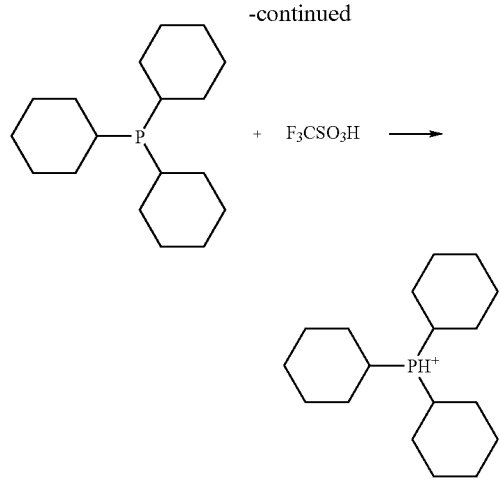

Spectroscopic Data:

300 MHz-$^1$H-NMR (CDCl$_3$): δ=1.2-1.5 (m, 9H); 1.5-1.7 (m, 6H); 1.7-1.85 (m, 3H); 1.85-2.0 (m, 6H); 2.0-2.15 (m, 6H); 2.45-2.58 (m, 3H); 6.07 (dm, 1H, $^1$J=474 Hz).

120 MHz-$^{31}$P-NMR (CDCl$_3$): δ=27.7.

Melting point (DSC): 225° C. (onset); decomposition (DSC): >350° C.

Example 2

Preparation of Tricyclohexyl Phosphonium Trifluoromethane Sulfonate from the Tricyclohexyl Phosphine Carbon Disulfide Adduct 80 ml of a solution of 116.7 g cyclohexylchloride in 390 ml of diethylether and 0.5 ml of 1,2-dibromoethane are added to 23.9 g of magnesium turnings, while the reaction mixture is heated to 41° C. The remaining cyclohexylchloride solution is slowly added to the mixture under reflux. After two hours of stirring at reflux the Grignard solution is diluted with 60 ml of tert-butylmethylether, added to a solution of 45.0 g of phosphorus trichloride in 170 ml tert-butylmethylether at −17 to −7° C. within 140 min, and stirred over night at room temperature. After one hour of stirring at reflux the mixture is added to 220 ml of 15% ammonium chloride solution at 10 to 38° C., and the paste-like lower phase is diluted with 140 ml of water. The lower aqueous phase is discarded, and to the upper organic phase are added 25.0 g of carbon disulfide. The resulting precipitated reddish-brown solid is filtered off, washed three times each with 50 ml of petrol ether, and dried at 35° C. under vacuum. 72.7 g (62%) of tricyclohexyl phosphine carbon disulfide adduct is obtained. 17.8 g of this tricyclohexyl phosphine carbon disulfide adduct is added to 100 ml of ethanol, and 96 ml of this mixture is distilled off. To the slightly opaque, yellowish melt is again added 100 ml of ethanol, and an additional 97 ml of solvent are distilled off. This process is repeated with 50 ml of ethanol and 49 ml of distillate. The tricyclohexyl phosphine released from the carbon disulfide in residue is taken up in 100 ml tert-butylmethylether, and added to 4.4 ml trifluoromethane sulfonic acid and additional 50 ml tert-butylmethylether for the dilution of the product suspension. The solid is filtered off, and dried at 40° C. The solid is filtered off, and dried at 40° C. 17.8 g (83%; 53% from phosphorus trichloride) colorless tricyclohexyl phosphonium triflate is obtained.

Example 3

Preparation of Tricyclohexyl Phosphonium Methane Sulfonate (PCy$_3$*H$_3$CSO$_3$H, C$_{19}$H$_{37}$O$_3$PS)

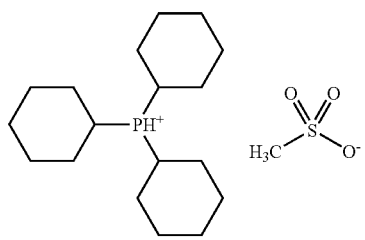

17.8 g tricyclohexyl phosphine carbon disulfide adduct is added to 100 ml ethanol, and 80 ml of this mixture is distilled off. The residue is successively taken up in 100 ml and 50 ml ethylacetate, and a total of an additional 163 ml of solvents are distilled off. The remaining melt is dissolved in 60 ml tert-butylmethylether, cooled down to 10° C., and 3.2 ml methane sulfonic acid are added. The colorless solid is filtered off after 15 min at 5° C., washed twice with 10 ml tert-butylmethylether each, and dried at 40° C. under vacuum. 14.3 g (76%) tricyclohexyl phosphonium methane sulfonate is obtained as a colorless, crystalline powder.

Spectroscopic Data:

300 MHz-$^1$H-NMR (CDCl$_3$): δ=1.2-1.5 (m, 9H); 1.5-1.7 (m, 6H); 1.7-1.85 (m, 3H); 1.85-2.0 (m, 6H); 2.0-2.15 (m, 6H); 2.45-2.59 (m, 3H); 2.82 (s, 3H); 6.82 (dd, 1H, $^1$J=489 Hz).

120 MHz-$^{31}$P-NMR (CDCl$_3$): δ=23.9.

Example 4

Tricyclohexyl Phosphonium P-Toluene Sulfonate (PCy$_3$*pTsOH, C$_{25}$H$_{41}$O$_3$PS)

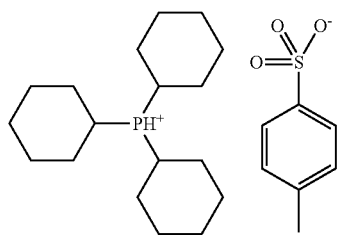

1.2 g (12 mmol) p-toluene sulfonic acid monohydrate is dissolved twice in 25 ml chlorobenzene each, and concentrated to dryness in order to remove the water aceotropically. The remaining residue is taken up in 25 ml diethylether and added to 25 ml of a solution of 12 mmol tricyclohexyl phosphine in diethylether. 4.2 g (77%) tricyclohexyl phosphonium p-toluene sulfonate is obtained as a colorless solid, which is filtered off and washed with diethylether.

Spectroscopic Data:

300 MHz-$^1$H-NMR (CDCl$_3$): δ=1.15-1.5 (m, 9H); 1.5-1.7 (m, 6H); 1.7-1.8 (m, 3H); 1.8-2.0 (m, 6H); 2.0-2.15 (m, 6H); 2.33 (s, 3H); 2.46-2.60 (m, 3H); 6.93 (dd, 1H, $^1$J=490 Hz); 7.14 (d, 2H); 7.80 (d, 2H).

120 MHz-$^{31}$P-NMR (CDCl$_3$): δ=22.9.
IR (KBr): $\bar{v}$ (cm$^{-1}$)=3445, 2928, 2855, 1601, 1450, 1215, 1196, 1119, 1030, 1011, 818, 679, 563.
Melting point (DSC): 140° C. (onset).

Example 5

Tricyclohexyl Phosphonium Trifluoride Acetate
(PCy$_3$*F$_3$CCO$_2$H, C$_{20}$H$_{34}$F$_3$O$_2$P)

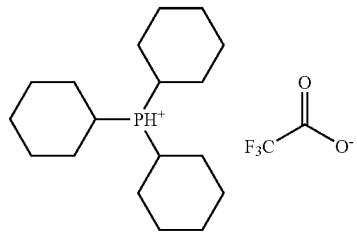

To 25 ml of a solution of 12 mmol tricyclohexyl phosphine prepared in diethylether (as in example 2) is added 1.4 g (12 mmol) trifluoride acetic acid. After some time, a crystalline solid is precipitated, which is filtered off, and washed with a little diethylether. 2.4 g (59%) of a colorless solid is obtained.
Spectroscopic Data:
300 MHz-$^1$H-NMR (CDCl$_3$): δ=1.25-1.5 (m, 9H); 1.5-1.7 (m, 6H); 1.7-1.85 (m, 3H); 1.85-2.0 (m, 6H); 2.0-2.05 (m, 6H); 2.44-2.57 (m, 3H); 6.24 (db, 1H, $^1$J=474 Hz).
120 MHz-$^{31}$P-NMR (CDCl$_3$): δ=26.9.
IR (KBr): $\bar{v}$ (cm$^{-1}$)=3425, 2936, 2858, 1736, 1639, 1450, 1192, 1146, 1007, 718.
Melting point (DSC): 95° C. (onset).

Example 6

Preparation of Tri-Tent-Butyl Phosphonium Trifluoromethane Sulfonate (PtBu$_3$T, PtBu$_3$*F$_3$CSO$_3$H, C$_{13}$H$_{28}$F$_3$O$_3$PS)

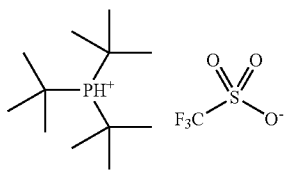

1265 g of a 45% tri-tert-butylphosphine solution in pentane prepared from phosphorustrichloride and tert-butyllithium is diluted under inert gas with 1380 ml anhydrous degassed diethylether. 198 ml trifluoromethane sulfonic acid is added to the solution at 0 to 5° C. while cooling. The forming suspension is stirred for one hour at 0° C., and the solid is filtered off, and dried at 50° C. under vacuum. 725.2 g of bright yellow solid is obtained. 725 g of the raw product is recrystallized from 1900 ml ethanol/diethylether 1:1, and the crystals are washed with 100 ml diethylether. After drying under vacuum at 50° C., 539.6 g (74%) of colorless tri-tert-butylphosphonium trifluoromethane sulfonate is obtained. The reaction is schematically illustrated below:

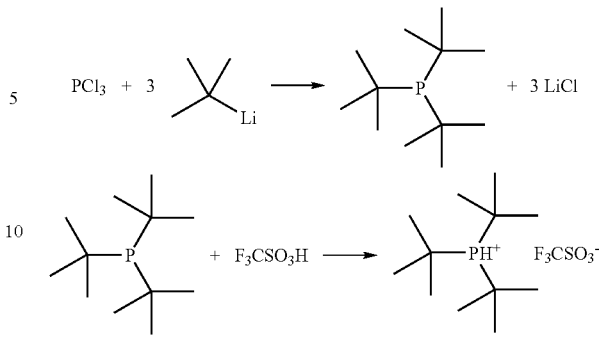

Spectroscopic Data:
300 MHz-$^1$H-NMR (CDCl$_3$): δ=1.67 (d, 27H, $^3$J=16 Hz); 6.52 (d, 1H, $^1$J=465 Hz).
120 MHz-$^{31}$P-NMR (CDCl$_3$): δ=49.9.
Melting point (DSC): 175° C. (onset).

Example 7

Tricyclohexyl Phosphonium Fluorosulfonate
(PCy$_3$*FSO$_3$H, C$_{18}$H$_{34}$FO$_3$PS)

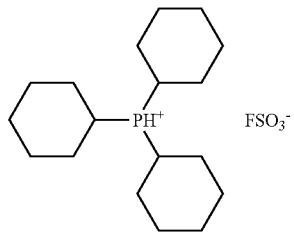

0.7 ml (12 mmol) fluorosulfonic acid is added to 25 ml of a solution of 12 mmol tricyclohexyl phosphine in diethylether prepared as in example 2. The product precipitates with a strong exotherm. 4.8 g of a colorless solid is obtained.
Spectroscopic Data:
300 MHz-$^1$H-NMR (CDCl$_3$): δ=1.2-1.5 (m, 9H); 1.5-1.7 (m, 6H); 1.7-1.85 (m, 3H); 1.85-2.0 (m, 6H); 2.0-2.15 (m, 6H); 2.47-2.590 (m, 3H); 5.97 (dd, 11-1, $^1$J=473 Hz).
120 MHz-$^{31}$P-NMR (CDCl$_3$): δ=28.2.
IR (KBr): $\bar{v}$ (cm$^{-1}$)=3449, 2936, 2858, 1639, 1450, 1273, 1065, 1007, 714, 579.
Melting point (DSC): 136° C. (onset).

The preparation of phosphines, phosphine adducts, or phosphonium salts, respectively, according to the prior art is described in the following comparative examples:

Comparative Example 1

Tricyclohexyl Phosphonium Chloride (PCy$_3$*HCl, C$_{18}$H$_{34}$ClP, CAS-Nr.: 98297-67-7)

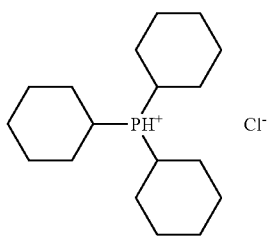

225 g cyclohexyl chloride and 750 ml diethylether are mixed. 100 ml of this mixture is added to 48.0 g magnesium turnings, and the reaction is started by adding 1 ml 1,2-dibromethane. The remaining cyclohexyl chloride mixture is added to the magnesium turnings within 3.5 hours under cooling at 38-40° C. The suspension is stirred again for one hour, cooled down to room temperature, and the cyclohexyl magnesium chloride solution is decanted from the remaining magnesium turnings. 156.7 g of the Grignard solution obtained in this manner is mixed with 120 ml tetrahydrofuran and slowly added to a mixture of 18.1 g phosphorus trichloride and 60 ml tetrahydrofuran at −20° C., and to an additional 100 ml tetrahydrofuran 20° C. After one hour of stirring at 37° C., the reaction mixture is added to 110 ml of a 15% ammonium chloride solution in water and 70 ml water at 20° C. The lower phase is separated and discarded. To the organic phase is added 10.1 g carbon disulfide. During this process, a reddish-brown precipitate is obtained, which is filtered off after 3 days, and washed three times each with 20 ml petrolether. After drying the solid at 35° C. under vacuum, 25.4 g (54%) of a tricyclohexylphosphine carbon disulfide adduct (CAS-Nr.: 4635-58-9) is obtained as a reddish-brown solid. From a mixture of 17.8 g of the tricyclohexyl phosphine carbon disulfide adduct and 100 ml ethanol, 80 ml of solvent is distilled off at 78-79° C. The oily residue is taken up in 80 ml tert-butylmethylether, and the tricyclohexyl phosphine solution is treated with hydrogen chloride at 20° C. The resulting suspension is diluted with 70 ml tert-butylmethylether. After complete precipitation of the tricyclohexyl phosphine as hydrochloride salt the solvent is evaporated off, and the solid residue is taken up in 100 ml tert-butylmethylether. The solid is filtered off, washed twice with 10 ml tert-butylmethylether each, and dried at 0.02 mbar. 13.1 g of a colorless hygroscopic solid is obtained. It contains 22.5% chloride so that it is assumed that in addition to the hydrochloride an additional equivalent hydrogen chloride is bound in the crystal (calculated for $PCy_3*2$ HCl: 20.1% chloride). If a sample of the solid is left at open atmosphere, it will melt after one hour.

Spectroscopic Data:
300 MHz-$^1$H-NMR (CDCl$_3$): δ=1.2-1.5 (m, 9H); 1.5-1.7 (m, 6H); 1.7-1.8 (m, 3H); 1.8-2.0 (m, 6H); 2.0-2.15 (m, 6H); 2.49-2.62 (m, 3H); 7.00 (dd, 1H, $^1$J=479 Hz).
120 MHz-$^{31}$P-NMR (CDCl$_3$): δ=24.2.
Melting point (DSC): 118° C. (onset).

Comparative example 2

Tricyclohexyl Phosphonium Chloride

An attempt to precipitate the hydrochloride with concentrated hydrochloric acid from the water containing tricyclohexyl phosphine solution in THF, which was obtained as in example 1, and to isolate it as a solid failed due to the fact that the very hygroscopic oily material did not dry, even over phosphorus pentoxide.

Comparative Example 3

Tricyclohexyl Phosphonium Bromide (PCy$_3$*HBr, C$_{18}$H$_{34}$BrP, CAS-Nr.: 20515-47-3)

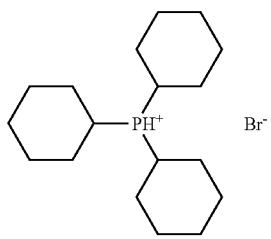

17.8 g tricyclohexyl phosphine carbon disulfide adduct are taken up in 100 ml ethanol, and the solvent is distilled off. The residue is taken up in 100 ml ethanol, the solution is concentrated, and once again taken up in 50 ml ethanol and concentrated. The tricyclohexyl phosphine released from the carbon disulfide is dissolved in 100 ml diethylether. Anhydrous hydrogen bromide, generated from 5 g tetraline, 0.1 g iron powder, and 1 ml bromine, is introduced into 25 ml of this solution containing 12 mmol tricyclohexyl phosphine. A crystalline solid precipitates immediately, which is filtered off, and washed with ether. 4.4 g of a very hygroscopic colorless solid is obtained.

Spectroscopic Data:
300 MHz-$^1$H-NMR (CDCl$_3$): δ=1.2-1.5 (m, 9H); 1.5-1.75 (m, 6H); 1.75-1.85 (m, 3H); 1.85-2.0 (m, 6H); 2.1 (m, 6H); 2.55-2.68 (m, 3H); 7.35 (dd, 1H, $^1$J=479 Hz).
120 MHz-$^{31}$P-NMR (CDCl$_3$): δ=21.6.
IR (KBr): $\bar{v}$ (cm$^{-1}$)=3402, 2932, 2855, 1636, 1447, 1011.
Melting point (DSC): 108° C. (onset).

Comparative Example 4

Tricyclohexyl Phosphonium Hydrogen Sulfate (PCy$_3$*H$_2$SO$_4$, C$_{18}$H$_{35}$O$_4$PS)

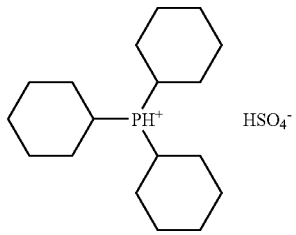

1.2 g (12 mmol) concentrated sulfuric acid are added to 25 ml of a solution of 12 mmol tricyclohexyl phosphine in diethylether prepared as in comparative example 3. The initially formed smudgy mass crystallizes over time, and can then be filtered off. 4.5 g of a colorless hygroscopic solid is obtained.

Spectroscopic Data:
300 MHz-$^1$H-NMR (CDCl$_3$): δ=1.15-1.5 (m, 9H); 1.5-1.7 (m, 6H); 1.7-1.8 (m, 3H); 1.8-1.95 (m, 6H); 2.05 (m, 6H); 2.48-2.62 (m, 3H); 6.22 (dd, 1H, $^1$J=482 Hz); 10.96 (s, 1H).
120 MHz-$^{31}$P-NMR (CDCl$_3$): δ=25.7.
IR (KBr): $\bar{v}$ (cm$^{-1}$)=3425, 2932, 2855, 1636, 1450, 1223, 1192, 1080, 1049, 1007, 891, 590.
Melting point (DSC): 189° C. (onset).

Comparative Example 5

Tricyclohexyl Phosphonium Perchlorate (PCy$_3$*HClO$_4$, C$_{18}$H$_{34}$ClO$_4$P)

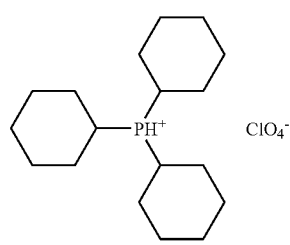

1.1 ml (12 mmol) perchloric acid is added to 25 ml of a solution of 12 mmol tricyclohexyl phosphine in diethylether prepared as in comparative example 3. Under a slight heat development a crystalline solid precipitates immediately, which is filtered off, and washed with diethylether. 3.4 g of a colorless solid is obtained. This solid is an explosive due to a shock sensitivity at an impact energy of 25 J.

Spectroscopic Data:

300 MHz-$^1$H-NMR (CDCl$_3$): δ=1.25-1.5 (m, 9H); 1.5-1.7 (m, 6H); 1.7-1.85 (m, 3H); 1.8-2.0 (m, 6H); 2.05 (m, 6H); 2.48-2.62 (m, 3H); 5.86 (dd, 1H, $^1$J=468 Hz).

120 MHz-$^{31}$P-NMR (CDCl$_3$): δ=28.9.

IR (KBr): $\bar{v}$ (cm$^{-1}$)=3425, 2932, 2858, 1655, 1450, 1088, 1007, 621.

Melting point (DSC): 184° C. (onset); decomposition (DSC): 204° C. (onset, 376 J/g).

Comparative Example 6

Tricyclohexyl Phosphonium Tetrafluoroborate (PCy$_3$*HBF$_4$, C$_{18}$H$_{34}$BF$_4$P)

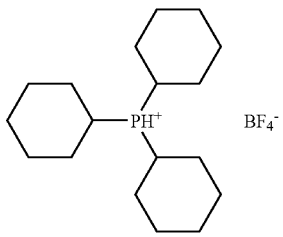

217 g of a Grignard solution prepared as in comparative example 1) is mixed with 60 ml tert-butylmethylether, and slowly added to a mixture of 23.6 g phosphorus trichloride and 60 ml tert-butylmethylether at −20° C. to −10° C. The suspension is stirred for one hour at 40° C., and is added to a 15% ammonium chloride solution in water and 85 ml water at 4° C. to 22° C. The lower phase is separated and discarded. 27.3 g tetrafluoroboric acid (54% in diethylether) are added to the organic phase. A precipitate forms, which is filtered off after one hour, and is washed twice each with 20 ml tert-butylmethylether. The filter cake is dried in a porcelain dish in a convection oven at 40° C. 47 g of a colorless solid with a melting point of 164-166° C. is obtained.

Spectroscopic Data:

300 MHz-$^1$H-NMR (CDCl$_3$): δ=1.2-1.5 (m, 9H); 1.5-1.7 (m, 6H); 1.7-1.85 (m, 3H); 1.85-2.0 (m, 6H); 2.0-2.1 (m, 6H); 2.44-2.57 (m, 3H); 5.85 (dd, 1H, $^1$J=474 Hz).

120 MHz-$^{31}$P-NMR (CDCl$_3$): δ=28.6.

Melting point (DSC): 165° C. (onset).

The trialkylphosphonium salts according to the invention are used in a multitude of coupling reactions. A connection of two alkyl or aryl groups is a coupling reaction in the invention; see March, Advanced Organic Chemistry, 4$^{th}$ Ed., page 449, paragraph A (Two hydrocarbon radicals are thus coupled with the aid of a metal containing catalyst). Examples for these are the reactions according to Buchwald, Heck, Negishi, Stille, Sonogashira, and Suzuki.

The use of the phosphonium salts according to the invention is explained in further detail below, without limiting the invention to the same:

Application Example 1

Use of the Tri-Tert-Butylphosphonium Salts According to the Invention in Reactions According to Suzuki 35.2 mg tris-(dibenzylidenaceton)-dipalladium(0), 28.2 mg tri-tert-butylphosphonium trifluoromethane sulfonate (PtBu$_3$T), 1264 mg 4-methoxybenzene boronic acid and 1472 mg potassium fluoride are dissolved in 14.4 ml tetrahydrofuran in a flask that has been rendered inert. After 5 minutes 984 µl 4-chloroacetophenon are added slowly to this mixture. After 16 hours of stirring at 28° C. the product mixture was diluted with 20 ml tetrahydrofuran, filtered on silica gel, and the same was re-washed with 30 ml tetrahydrofuran. The solution is concentrated to dryness under vacuum. The product is purified by silica gel chromatography with a methylene chloride/hexane mixture, wherein the ratio of methylene chloride to hexane is between 1:1 to 4:1. 0.63 g (38%) of 4-acetyl-4'methoxybiphenyl is obtained.

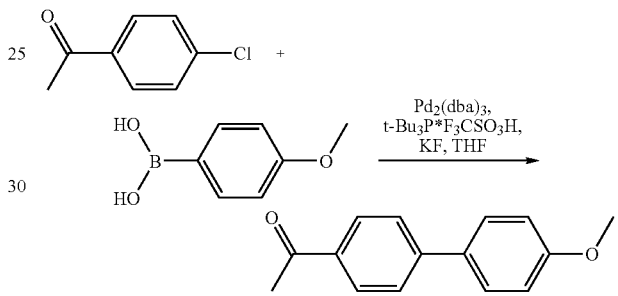

This example illustrates that better yields can be obtained with tri-tert-butyl phosphonium trifluoromethane sulfonate as the ligand precursor, than with tri-tert-butyl phosphonium tetrafluoroborate known to prior art, and listed in comparative use 1.

The following comparative examples describe the use of phosphines, phosphine adducts, or phosphonium salts, respectively, according to the prior art:

The use of tricyclohexyl phosphonium tetrafluoroborate in a coupling reaction according to Suzuki (M. R. Netherton, G. C. Fu, Org. Lett. 2001, 3, 4295-4298) is described below:

Comparative Use 1

26.4 mg tris-(dibenzylideneacetone)-dipalladium(0), 17.4 mg tri-tert-butylphosphonium tetrafluoroborate, 948 mg 4-methoxybenzene boronic acid and 1104 mg potassium fluoride are dissolved in 10.8 ml tetrahydrofuran in a flask rendered inert. After 5 minutes 738 µl 4-chloroacetophenon are added slowly to this mixture. After 21 hours of stirring at 28° C. the product mixture is diluted with 15 ml tetrahydrofuran, filtered on silica gel, and the same is extracted with 30 ml tetrahydrofuran. The solution is concentrated to dryness under vacuum. The product is purified by silica gel chromatography with a methylene chloride/hexane mixture, wherein the ratio of methylene chloride to hexane is between 1:1 to 4:1. 0.43 g (34%) of 4-ccetyl-4'methoxybiphenyl is obtained. The comparison of the compound according to the invention with those of prior art resulted in the following:
1. The yield obtained in the Suzuki reaction with the compound of the invention is 38% while the tetrafluoroborate provided only 34%.

2. The corrosion characteristics are superior with the compounds of the invention. The wett tricyclohexyl phosphonium tetrafluoroborate from the precipitation in the comparative example 6 and the wet trialkylphosphonium salts from examples 1 to 6 according to the invention were dried in a porcelain dish at an elevated temperature. The glazing of the porcelain dishes after drying of the compounds of the examples according to the invention had the same condition as before, while the glazing of the porcelain dish, in which the tricyclohexyl phosphonium tetrafluoroborate was dried, was matte, and substantially affected by corrosion. This example illustrates that as opposed to sulfonates and carboxylates, phosphonium tetrafluoroborates have a strong corrosive characteristic, and therefore when used in glass or enameled apparatuses lead to an undesired, accelerated wear of these types of apparatuses.

The above results show that it is possible to provide phosphonium salts which provide high yields and are not corrosive.

The invention claimed is:

1. A method of coupling a monophosphonium salt in coupling reactions together with one or more transition metals or their compounds, wherein the monophosphonium salt is of the type $PR^1R^2R^3*ZR'$, wherein:
   residues $R^1$, $R^2$, $R^3$ are selected from the group consisting of H, alkyl residues, cycloalkyl residues, aryl residues, and hetaryl residues, and wherein hydrogen atoms may be substituted in the alkyl residues, cycloalkyl residues, aryl residues or hetaryl residues;
   $R^1$, $R^2$, $R^3$, and $R'$ can be the same or different;
   Z is selected from the group consisting of —$SO_3H$ and —COOH;
   the residue $R'$ when Z is —$SO_3H$ is selected from the group consisting of alkyl residues, cycloalkyl residues, aryl residues, hetaryl residues and halogens, and wherein hydrogen atoms may be substituted in the alkyl residues, cycloalkyl residues, aryl residues or hetaryl residues;
   the residue $R'$ when Z is —COOH is selected from the group consisting of H, alkyl residues, cycloalkyl residues, aryl residues and hetaryl residues, and wherein hydrogen atoms may be substituted in the alkyl residues, cycloalkyl residues, aryl residues or hetaryl residues.

2. The method according to claim 1, wherein $R^1$, $R^2$, and $R^3$ are selected from the group consisting of alkyl residues and cycloalkyl residues.

3. The method according to claim 1, wherein the cycloalkyl residue is a cyclohexyl residue.

4. The method according to claim 1, wherein the alkyl residue is a tert-butyl residue.

5. The method according to claim 1, wherein $R'$ is selected from the group consisting of —$CH_3$, —$CX_3$, and an aryl residue, wherein X is a halogen, and the aryl residue is methylphenyl.

6. The method according to claim 1, wherein Z is —$SO_3H$.

7. The method according to claim 1, wherein the monophosphonium salt is selected from the group consisting of tricyclohexyl phosphonium trifluoromethane sulfonate, tricyclohexyl phosphonium methane sulfonate, tricyclohexyl phosphonium p-toluene sulfonate, tricyclohexyl phosphonium trifluoroacetate, tri-tert-butylphosphonium trifluoromethane sulfonate, tri-tert-butylphosphonium methane sulfonate, tri-tert-butylphosphonium p-toluene sulfonate, tri-tert-butylphosphonium trifluoroacetate, and mixtures thereof.

8. The method according to claim 1, wherein the transition metals are selected from the group consisting of the elements of the seventh and eighth subgroup of the periodic table and combinations thereof.

9. The method according to claim 8, wherein the transition metals are selected from the group consisting of rhenium, ruthenium, rhodium, palladium, osmium, indium, platinum and combinations thereof.

10. The method according to claim 1, wherein the phosphine of the phosphonium salt is released by adding a base.

11. The method according to claim 1, wherein the coupling reaction is selected from the group consisting of a reaction according to Buchwald, Heck, Negishi, Stille, Sonogashira, and Suzuki.

12. The method according to claim 5, wherein X is fluorine.

13. The method according to claim 5, wherein the aryl residue is methylphenyl.

14. The method according to claim 1, wherein the phosphine of the phosphonium salt is released by adding a metal alcoholate or an amine.

15. The method according to claim 1, wherein the phosphine of the phosphonium salt is released by adding sodium-tert-butylate.

* * * * *